United States Patent [19]

Bowman

[11] 4,314,484
[45] Feb. 9, 1982

[54] SELF-COMPENSATING OPTICAL DROP COUNT APPARATUS FOR MEASURING VOLUMETRIC FLUID FLOW

[75] Inventor: Robert J. Bowman, Salt Lake City, Utah

[73] Assignee: University of Utah Research Foundation, Salt Lake City, Utah

[21] Appl. No.: 83,002

[22] Filed: Oct. 9, 1979

[51] Int. Cl.³ .................... G01F 13/00; A61M 5/00
[52] U.S. Cl. ........................ 73/861.41; 128/214 E; 128/DIG. 13
[58] Field of Search ............... 73/861.41; 128/214 E, 128/DIG. 13; 250/205, 222 PC, 573

[56] References Cited

U.S. PATENT DOCUMENTS

| 3,563,090 | 2/1971 | Deltour | 73/861.41 |
| 3,593,579 | 7/1971 | Hindman | 73/861.41 |
| 3,890,968 | 6/1975 | Pierce | 73/861.41 |
| 4,038,982 | 8/1977 | Burke et al. | 128/214 |
| 4,105,028 | 8/1978 | Sadlier | 73/861.41 X |
| 4,173,224 | 11/1979 | Marx et al. | 128/214 |
| 4,181,130 | 1/1980 | Bailey | 128/DIG. 13 |

Primary Examiner—Herbert Goldstein

Attorney, Agent, or Firm—Thorpe, North, Western & Gold

[57] ABSTRACT

A self-compensating optical drop count apparatus for measuring volumetric fluid flow by optically counting the number of drops of fluid that pass through a drop chamber, each drop being formed so as to be of approximate equal volume. Optical counting circuitry is designed to count each drop only once. The count is accumulated in a holding register where it may interface with external instrumentation equipment adapted to display the count and/or convert it to a volumetric measurement by multiplying it by the average volume of fluid contained in each drop. A compensation technique is utilized to maintain the intensity of a light beam, through which the drops must pass, at a constant level. Compensation is achieved in a closed loop system which varies the drive current to the light emitter to compensate for long-term variations that occur in the intensity of the light beam as sensed at a light detector. Compensation techniques are also utilized in converting the count to a volumetric measurement to account for known changes in drop volume as a function of drop rate.

19 Claims, 6 Drawing Figures

SELF-COMPENSATING OPTICAL DROP COUNT APPARATUS FOR MEASURING VOLUMETRIC FLUID FLOW

BACKGROUND OF THE INVENTION

1. Field of the Invention

This application relates to a fluid flow measuring apparatus, and more particularly to a self-compensating optical drop count apparatus for measuring volumetric fluid flow of low pressure fluids.

2. Description of the Prior Art

The need for an accurate in-line volumetric fluid flow measurement apparatus has long existed. When fluid is being transferred from one storage area to another through a tube, pipe, or similar line, it is useful to know exactly how much fluid has been transferred without the need of removing the transferred fluid from the line and measuring it in containers of known volume.

In-line fluid flow measurement devices usually require that the fluid being measured by under sufficient pressure to activate some sort of monitoring device, such as a paddle wheel, that is inserted in the line. Such monitoring devices not only require that the fluid be under pressure, but they also tend to impede the normal fluid flow. Such devices are thus ill suited for low pressure fluid flow applications.

Recent advances in medical technology have demonstrated a critical need for accurate real time measurements of body fluids for patients in hospitals and other health care facilities. Such fluids, which are usually under very low pressure, may be infused into the patient or excreted from the patient. Moreover, the fluids rate is typically drops of fluid rather than a constant stream. Also, because of the medical environment involved, only a closed measurement system can be used—i.e., one that does not violate the integrity of protection against bacterial infection.

Prior art systems for measuring body fluid flow have consisted primarily of monitoring the decrease in volume of a supply of fluid, in the case of fluids being infused into the body (such as blood or plasma), over a period of time. Correspondingly, in the case of fluids being excreted from the body (such as urine), fluid flow is typically measured by monitoring the increase in volume over a period of time in a reservoir, or other type of collection bag, where the excreted fluids are deposited. Other prior art systems weigh the fluid over a period of time. In all cases, the measurement is not a "real-time" measurement in the sense that a significant time period must usually pass before a meaningful measurement can be made.

With the advent of optical electronics, attempts have been made to measure the volume of fluid flow by optically sensing and counting the number of drops that pass through a drop chamber. When these drops of fluid are relatively uniform in volume, volumetric fluid flow is, in theory, easily derived from the drop count by merely multiplying the drop count by the known average volume per drop. However, numerous problems have been encountered with this approach. For one, the volume of fluid in each drop is not necessarily uniform, but may vary with the drop rate, a fast drop rate producing drops with more fluid volume than a slow drop rate. Also, there have been problems with maintaining the integrity of the light beam that must pass through the drop chamber where the drops are falling. Splashing of the fluid after the drops have fallen, as well as condensation that occurs within the drop chamber, or foreign matter on the outside off the chamber, tend to block the light beam, or reduce its intensity, so that it can no longer accurately sense the drops passing through the chamber. Also, the drop may break up into two or more drops as it falls, thereby causing a false count condition to exist.

SUMMARY OF THE INVENTION

A principle object of the present invention is to provide an optical drop count apparatus that is self-compensating so as to mitigate the effects of splashing and condensation within the drop chamber; and more particularly to compensate the intensity of the light beam so that the average long-term intensity of the beam after it has passed through the drop chamber (and necessarily after it has also passed through any condensation or liquid that has splashed on the walls of the drop chamber) is maintained at a constant level.

Another principle object off the present invention is to provide an optical drop count apparatus that compensates for changes in the volume of fluid in each drop attributable to changing drop rates.

A further object of the present invention is to provide an accurate self-compensating drop count apparatus that is simple to operate and maintain, and that is further compensated to guard against false counts as a drop falls through the drop chamber.

Another object of the present invention is to provide a self-compensating drop count apparatus that is compatible with the measurement of low pressure fluids.

A still further object of the invention is to provide such a self-compensating drop count apparatus, in accordance with one embodiment thereof, that is compatible with the measurement of volumetric fluid flow of animal and human body fluids, thereby allowing the apparatus to be used for medical applications.

An additional object of the present invention is to provide such a self-compensating optical drop count apparatus that is easily transportable, thereby allowing it to be placed adjacent to the source of the fluids being measured.

Still a further object of the present invention, in accordance with a medical application thereof, is to provide an accurate, reliable self-compensating optical drop count apparatus that is ideally suited for the closed environment of medical applications, allowing the use of disposable drop count chambers and tubing.

Still another object of the present invention is to provide a drop count apparatus that may be interfaced with computing systems which can be programmed to convert the drop count to the volume of fluid that has dropped through the drop chamber, thereby providing a real-time measurement of the volume of fluid that has flowed through the apparatus.

A still further object of the present invention is to provide a drop count apparatus, in accordance with another embodiment thereof, that can be easily multiplied throughout a complex system in which the flow of numerous fluids must be monitored and measured, but each of which interfaces with a single common computer or computing system.

The above and other objects of the present invention are realized in an embodiment of an optical drop count apparatus that includes a drop chamber through which the fluid to be measured must pass. Fluid enters the drop chamber through suitable hosing, tubing, channeling, or the like, which is connected to the source of the fluid. Prior to entering the drop chamber, the fluid passes through an orifice of fixed dimensions. This orifice serves to separate the fluid into drops of approximate uniform volumetric size.

Also connected to the drop chamber is outlet hosing, tubing, channeling, or the like that carries the fluid after it has dropped through the drop chamber to a suitable destination.

The drop chamber is fabricated so that a light beam may be directed laterally therethrough from a light emitter on one side to a light detector on the other side. This is accomplished by constructing the drop chamber so that the walls thereof are either transparent, or at least translucent of sufficient degree, to allow the light beam from the light emitter to pass through these walls and be received by the light detector on the other side. Alternatively, the walls of the drop chamber could be made of an opaque material with windows therein that would allow the light beam to laterally pass through the windows and thus through the chamber.

The light beam from the light emitter passes through the chambers so as to intersect with the drop path of the drops of fluid which are longitudinally dropping through the chamber. Each time a drop passes through the chamber it interrupts the light beam from the light emitter. The light detector, which generates an output signal to indicate the presence and intensity of the light beam, senses when the light beam has been interrupted by a drop of fluid. In effect, each time the light beam is interrupted by a drop of fluid, the output signal from the light detector produces a pulse. This pulse, after being properly amplified, and buffered, is counted by electronic counting circuitry. The counting ciruitry may be interfaced with external instrumentation equipment, such as a computer or micro-processor system, so that the count can be converted to a measure of the volume of fluid that has passed through the drop chamber.

Compensation of the light beam's intensity is accomplished by the use of an integrater that monitors the output signal from the light detector. The time constant of the integrater is sufficiently long so that fast interruptions of the light beam, as when drops fall through the drop chamber, are not sensed. However, long term variations in the intensity of the light beam are sensed, such as those that would be caused when splashed or condensed liquid accumulates on the walls of the drop chamber. The integrater senses these long term variations in the intensity of the light beam and produces an output control signal that controls the current that flows to the light emitter, thus, maintaining the intensity of the light beam sensed at the light detector, at a constant level.

Additional compensation to the light detector's output pulse signal is accomplished by triggering a timing circuit when a drop is first sensed. This timing circuit blocks any further pulses from being counted for a length of time roughly equal to the time it takes a drop to pass through the chamber, thereby guarding against false counts and ensuring that only one pulse is counted for each drop.

Further compensation for changes in the volume of drops is achieved by monitoring the drop rate and by compensating the drop count or volume per drop accordingly. Such compensation is ideally performed in the software of the external instrumentation equipment that computes volumetric flow from the drop count, but it may also be performed by hardware within the drop count apparatus itself.

BRIEF DESCRIPTION OF THE DRAWINGS

The above and other objects, features, and advantages of the invention will be more apparent from the following more particular description presented in connection with the accompanying drawings, in which.

DESCRIPTION OF THE PREFERRED EMBODIMENTS

Figure 1:
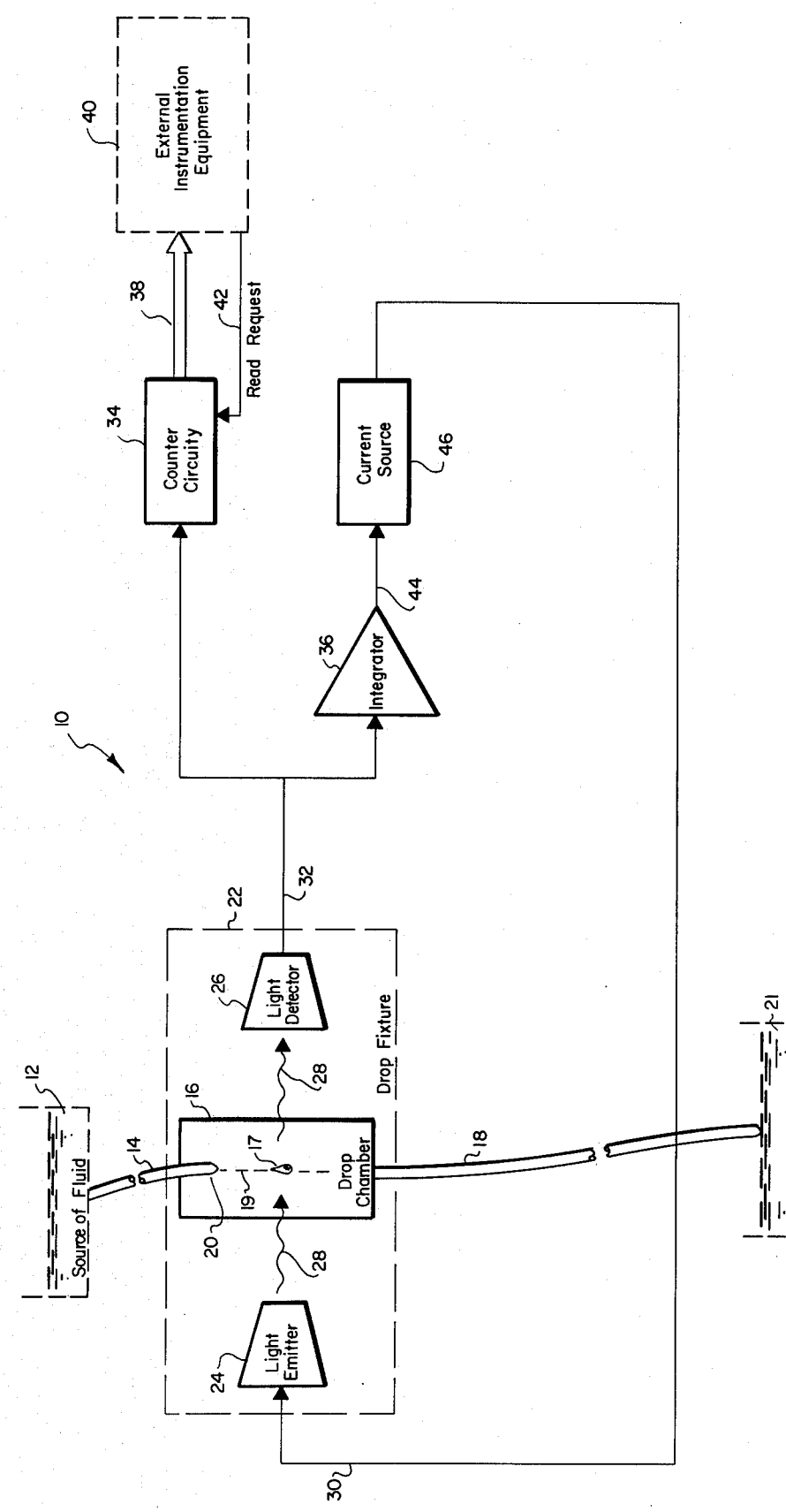
FIG. 1 is a block diagram of a self-compensating optical drop count apparatus for measuring volumetric fluid flow.

Referring to FIG. 1, there is shown generally at 10 an optical drop count apparatus that is self-compensating for measuring volumetric fluid flow. A source of fluid 12 is directed through inlet tubing or hosing 14 to a drop chamber 16. An orifice 20 is placed at the top of the drop chamber 16 and in series with the inlet tubing 14. The purpose of the orifice 20 is to block the fluid flowing through the tubing 14 until sufficient pressure is built up therewithin to cause a drop of fluid 17 to fall longitudinally through the drop chamber 16. Because the size of the orifice 20 is known and because the adhesion forces of the fluid 12 are relatively uniform, the amount of fluid included in each drop 17 will be approximately uniform. The amount of volume of fluid in each drop 17 can thus be calculated and verified through experimentation.

After passing through the drop chamber 16, the fluid 12 exits therefrom through suitable outlet tubing or hosing 18 to a desired destination 21.

In the preferred embodiment of the invention disclosed herein, it is anticipated that the drop chamber will be positioned so that the force of gravity causes the drop 17 to fall longitudinally therethrough along a well known and consistent drop path (shown symbolically as the dotted line 19).

The drop chamber 16 is one element of a drop fixture 22, which includes, in addition to the drop chamber 16, a light emitter 24 positioned to one side of the drop chamber 16, and a light detector 26, positioned on the opposite side of the drop chamber. The light emitter 24 produces a beam of light, shown symbolically as the wavy arrow 28, that is directed through the drop chamber 16 to the light detector 26. For purposes of this application, "light" is used to describe any forms of electro-magnetic radiation, including visible light, infrared, ultraviolet, and other sources of such radiation. The light beam 28 is produced in response to an input control signal that is sent to the light emitter 24 on signal line 30 (hereinafter referred to as the control signal 30). This control signal 30 controls the intensity of the light beam 28. Typically this control signal will be a current and the light emitter 24 will be a light emitting diode. As the amount of current that flows through the light emitting diode is increased, the intensity of the light beam 28 correspondingly increases.

The light detector 26 senses the presence and intensity of the light beam 28. Typically, this light detector will be a photosensitive transistor that generates an output signal on line 32 which indicates the presence and intensity of the detected light 28.

The output signal on line 32 (hereinafter referred to as output signal 32) is directed to counter circuitry 34 and an integrater 36. The counter circuitry 34 buffers, conditions, and amplifies the light detector's output signal and counts the number of pulses that occur in this signal. A pulse will occur in the output signal 32 everytime that a drop of fluid 17 interrupts the light beam 28. By counting these pulses, a count is obtained of the total number of drops 17 that have passed through the drop chamber 16, which count is accumulated in a register so that it may be read periodically. The output of this register is directed over count lines 38 to suitable external instrumentation equipment 40. This equipment may be simply a read out device to indicate the total drop count; or, in sophisticated embodiments of the invention, it may be computer instrumentation equipment that converts the drop count to a volumetric flow measurement. In either event, a read request line 42 is directed to the counter circuitry 34 to enable data to pass over the count line 38.

The integrater 36 monitors the output signal 32 from the light detector 26. The time constant of the integrater 36 is selected so that it will sense long-term variations in the amplitude of the signal 32. For purposes of this application, "long-term" signifies times greater than the time it takes a drop 17 to pass through the drop chamber 16. Thus, the integrater 36 is designed so that it is insensitive to the relatively short interruptions in the light beam 28 caused by the fluid 12 dropping through the drop chamber 16. However, should there be condensation on the walls of the drop chamber 16, or should the fluid, after dropping therethrough splash so as to obscure the walls of the chamber 16, and thereby reduce the amount of light that can pass therethrough, the integrater would thus sense this change in amplitude of the output signal 32.

If a variation is sensed in the amplitude of the output signal 32, the intergrater 36 generates a correcting signal on line 44 (hereinafter correcting signal 44) that is directed to a current source 46. The current source 46 responds to this correcting signal 44 and generates an output current proportional thereto, which current is sent to the light emitter 24 over signal line 30, and thus becomes the control signal 30 referred to previously. Thus, in operation, the integrater 36, the current source 46, the light emitter 24, and the light detector 26 form a closed loop system that maintains the intensity of the light beam 28 (as sensed at the light detector 26) at a constant level. Maintaining this detected light at a constant level ensures that the overall system operates as designed. That is, the pulses formed in the output signal 32 will always be of the same amplitude, and can thus always be counted the same, regardless of condensation, splashing or other impurities (inside or outside of the chamber) that might impede the light beam 28.

Figure 2:
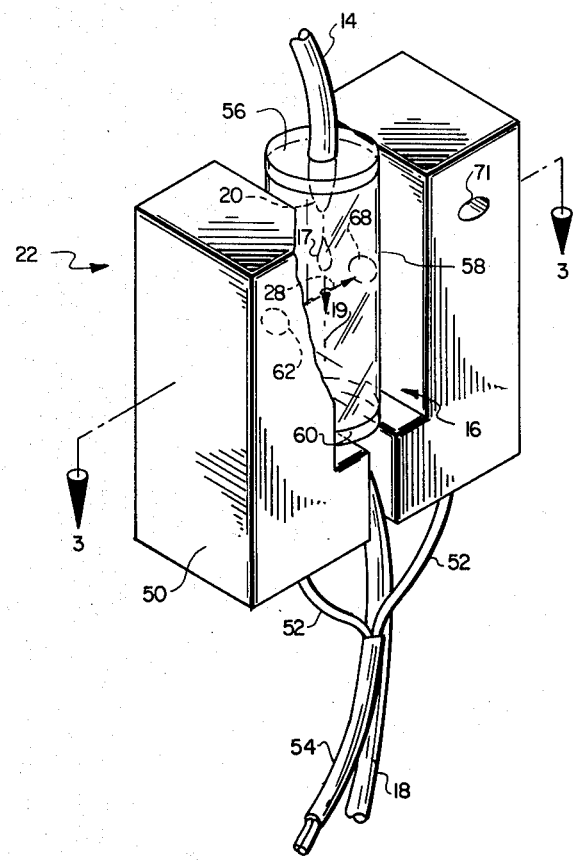
FIG. 2 is a perspective view of one possible embodiment of the drop fixture of FIG. 1, with a portion of the drop fixture cut away.
Figure 3:
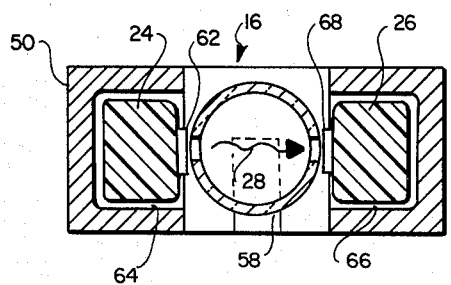
FIG. 3 is a cross sectional view taken along the line A—A in FIG. 2.

Referring now to FIGS. 2 and 3, there is shown respectively a perspective view of one embodiment of the drop fixture 22 and a cross-sectional view thereof. In FIG. 2, the drop chamber 16 is depected as a hollow chamber or tube 58, to which an upper end cap 56 and a lower end cap 60 have been placed. The inlet tubing 14 passes through the upper end cap 56 and the orifice 20 is placed at the end of the tubing 14 so as to cause the fluid to break unto drops 17 that pass longitudinally through the chamber along the path defined by the dashed line 19. Outlet tubing or hosing 18 is similiarly connected to the lower or bottom end cap 60 of the drop chamber 16 so as to provide a path whereby the fluid may be removed from the drop chamber 16.

Referring now to both FIGS. 2 and 3, the drop fixture 22 contains a light emitter 24, including a lens 62. The lens 62 serves to focus and direct the light beam 28 laterally through the drop chamber 16. The light emitter 24 is positioned inside an internal cavity 64 within a holding fixture 50 so that the lens 62 is adjacent to one side of the hollow chamber 58.

Likewise, the light detector 26 is inserted in a cavity area 66 within the fixture 50 so as to be on the opposite side of the drop chamber 16 from the light emitter 24. The light detector 26 is positioned within this cavity 66 so that its light receiving port 68 is directly opposite the lens 62 of the light emitter 24, with only the hollow chamber 58 separating the port 68 and the lens 62.

The signal lines associated with the input control signal 30 to the light emitter 24 and the output signal 32 from the light detector 26 are routed to these devices through appropriate wires 52, which are gathered together in a cable 54. This cable typically exits from the rear of the fixture 50 and is eventually directed to the counter circuitry 34, integrater 36, and other equipment. Also included in the drop fixture 50 is an indicator light 71 that signals when the drop count apparatus 10 is functional. The operation of this indicator lamp 71 will be explained more fully below. Appropriate control signals to control the indicator light 71 are included in the wires 52 and cable 54.

As indicated above, a preferred embodiment of the drop chamber 16 includes a hollow chamber 58 closed with end caps 56 and 60. The walls of this chamber may be either transparent, such as clear glass or plastic, or they may be translucent. For purposes of this application, "translucent" implies a substance through which light may be passed but in which the light is diffused more than it would be through a transparent material. Alternatively, the walls of the hollow chamber 58, could be comprised of an opaque material with windows inserted therein through which the light beam 28 could pass as it traveled from the light emitter 24 to the light detector 26.

Figure 4:
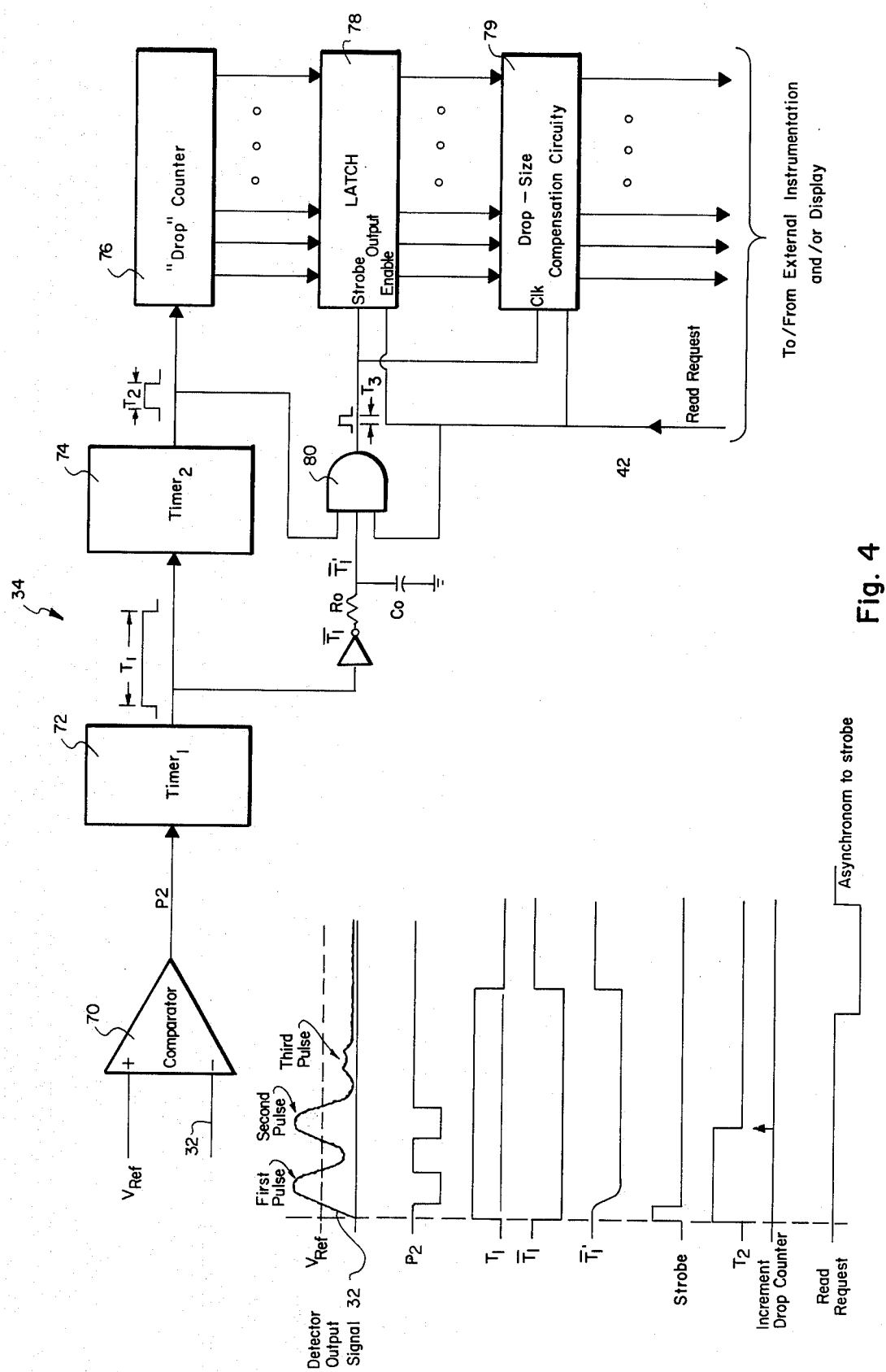
FIG. 4 is a functional block diagram of the counter circuitry of FIG. 1, including a timing diagram of the key signals associated therewith.

Referring now to FIG. 4, there is shown a functional block diagram of the counter circuitry 34. Included in the counter circuitry 34 is a comparator circuit 70, the output of which (labeled as P2 in FIG. 4) is directed to a first timer 72. The output of the timer 72 is directed to second timer 74. The output from the second timer 74 is directed to a counter 76. Outputs from the counter 76 are directed in parallel to a latch 78. Because the operation of the counter circuitry 74 is best explained with the use of a timing diagram, a timing diagram is included as part of FIG. 4.

In operation, the counter circuitry 34 functions as follows: the output signal 32 from the light detector 26 is directed to the comparator 70. This output signal 32 is compared in the comparator circuit which a reference voltage, labeled $V_{Ref}$. When the amplitude of the signal 32 exceeds the voltage $V_{Ref}$, the output signal P2 of the comparator goes low. Similarly, when the amplitude of the output signal 32 is less than the $V_{Ref}$, the output P2 of the comparator goes high. Thus, the function of the comparator 70 is to amplify, invert, and shape the output signal 32 from the light detector 26 so that a sharp, well-defined pulse is presented to the timer 72 each time a drop 17 interrupts the light beam 28.

It is to be noted in FIG. 4 that the output signal 32 appears as two large pulses followed by a third small pulse. Such is the typical response of the light detector to a single drop 17 that passes through the drop chamber 16. This is because the front edge of the drop 17, as it begins to interrupt the light beam 28, significantly scatters the light beam 28 so that very little light, if any, is sensed at the light detector 26 when little or no light is sensed by the detector 26, the output signal 32 goes high, thus causing the front part of the first large pulse. However, as the drop 17 continues to pass through the light beam 28, the drop itself serves to re-focus the light beam 28 so that much more light is detected at the light detector 26, causing the output signal 32 to go low, and thus creating the valley portion between the first and second pulses. If this valley portion is below the reference voltage, $V_{Ref}$, then the comparator circuit 70 will cause its P2 output signal to go high, as if the light beam had not been interrupted. As the drop continues to pass through the light beam 28, the back edge of the drop serves to scatter the light beam in the same fashion as the front edge of the drop did, thus causing the output signal 32 to go high again. Thus the second pulse shown in FIG. 4 is created.

The third pulse in FIG. 4 may or may not be present, but is caused by a small trailing drop which often follows the formation of a large drop through an orifice 20 of the type used herein. Whether this trailing drop is present or not, is of little consequence to the accuracy of the invention herein purposed, inasmuch as the volume of fluid contained in such a small trailing drop is not significant compared with the volume of fluid in the main or primary drop 17.

One of the functions of the counter circuitry 34 is to count these pulses generated in the output signal 32 as one count. This is achieved through the action of the timers 72 and 74. The timer 72 generates a pulse of a duration T1 seconds, as indicated in the timing diagram of FIG. 4. Time T1 is selected so as to be longer than the time it takes a drop 17 to pass through the drop chamber 16. The leading edge of this pulse T1 is used to trigger the second timer 74. Once triggered, timer 74 generates a pulse of duration T2 seconds, where T2 is significantly less than T1, as shown in FIG. 4. The trailing edge of this T2 pulse, is used to increment the counter 76. In this fashion, the counter 76 is incremented only once for each drop that passes through the drop chamber, even though the actual output signal from the light detector 26 may contain several pulses.

The latch 78 is "strobed," that is the contents of the drop counter 76 are loaded thereinto, each time the timers 72 and 74 are triggered. Likewise, the contents of the latch 78 are strobed into the drop-size compensation circuitry 79 at the same time. This strobbing is accomplished by generating a strobe pulse that is formed by ANDing the pulse T2 with the inverse of the pulse T1, after the edges of this inverse pulse have been significantly slowed down through the use of a filter network (shown in FIG. 4 as a resistor R0 and a capacitor C0, and in an AND gate 80. The output of the AND gate 80 is high so long as all of the inputs thereto are also high.

In this case, the inverse of the first pulse T1, after its edges have been slowed down, labeled T1', is considered high by the gate 80 for a time determined by the R0 and C0 values. Thus the output of the gate 80 is high for a corresponding time, labeled T3. T3 may be a very short time, e.g., on the order of 500 nsec., but it still achieves the desired strobbing function.

Also directed as an input to the gate 80 is a read request signal 42, which is received from external instrumentation equipment whenever the contents of the latch 78 are desired to be read. This request signal is asynchroness with the timing signals discussed thus far. However, when no read request signal is present, the read request signal 42 is high, thus enabling the gate 80 to perform its proper AND function with respect to the time impulses T2 and T1 as discussed above. When a read request is desired, the read request signal line 42 goes low, thus disabling the AND gate 80 and preventing the latch 78 from being strobbed while the external instrumentation equipment is reading the contents of the latch 78. If a read request signal occurs at the same time that a drop count is sensed, the counter 76 will still be incremented in the normal fashion, but the contents thereof will not be strobbed into the latch 78 until after the read request has been terminated and a subsequent drop is sensed to trigger timer 72 and 74.

Because the volume of fluid in a drop is a function of the drop rate, with a slow rate producing smaller drops than a fast rate, drop-size compensation circuitry 79 is coupled to the latch 78, to compensate for this volume variation. Various approaches can be used to accomplish such compensation. In FIG. 4, the drop-size compensation circuitry 79 categorizes the drop rate as being fast, slow, normal, very fast, etc., by measuring the time between clock pulses (which clock pulses are the same as the strobe pulses generated by the gate 80, with one pulse being generated each time the timers 72 and 74 are triggered). If the drop rate is categorized as fast, then the drop count as received from the latch 78 is increased appropriately to account for the increased volume associated with said fast rate drops before said count is sent to external instrumentation equipment. Similarly, if the drop rate is categorized as slow, then the drop count is decreased appropriately to account for the decreased volume associated with said slow rate drops prior to presenting said drop count to external instrumentation equipment. The external instrumentation equipment converts this compensated drop count to a volumetric measure by multiplying it by the average volume of fluid per drop at a normal rate.

The drop-count compensation circuitry 79 as described above can be readily realized by those skilled in the art using commercially available components. Alternatively, this drop-count compensation function can be realized in the external instrumentation equipment by modifying the multiplication factor used to convert the drop count to volumetric flow. To compensate in this fashion, the external instrumentation equipment must be given some indication of the drop rate. This can be done by merely presenting the strobe signal from the gate 80 to the external instrumenation equipment (as indicated by the dashed signal line in FIG. 4).

Figure 5:
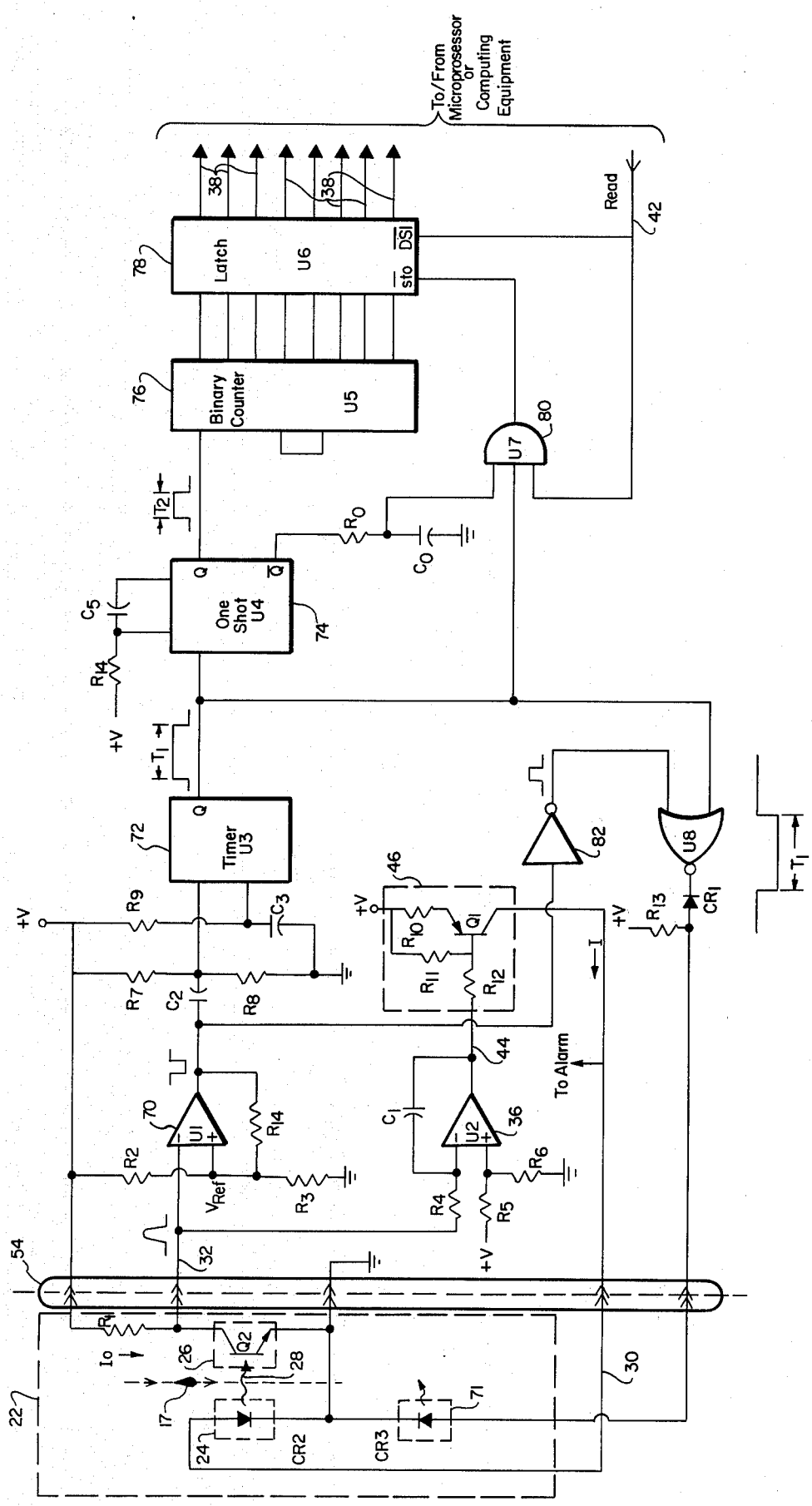
FIG. 5 is a more detailed logic schematic diagram showing one method of implementing the invention of FIG. 1.

Referring now to FIG. 5, there is shown a detailed schematic diagram of the present invention. While not all the detail required to make the invention is shown in FIG. 5, such as the power supply connections, there is sufficient detail shown to allow one skilled in the art to practice the invention. As FIG. 5 illustrates, the light emitter 26 is a light emitting diode, labeled as CR2. This diode may be a commercially available component, such as the TIL31 manufactured by Texas Instruments, Inc.

Optically coupled with the light emitter 24, is a light detector 26. As mentioned previously, this may be a photosensitive transistor Q2. A suitable component for the transistor Q2 is the TIL81, also manufactured by Texas Instruments. The collector of the photosensitive transistor Q2 is tied to a resistor R1 which is connected through suitable cabling 54 to a pull up voltage, $+V$. The emitter of the transistor Q2, as well as the cathode of the light emitting diode CR2, are connected to a common ground line that is connected to the ground of the circuitry through the cable 54. When a drop of fluid 17 is not interrupting the beam of light 28, the photo transistor Q2 is turned on so that a current $I_0$ flows therethrough. This current $I_0$ causes a voltage drop across R1 which voltage represents the output signal from the light detector 26. If the intensity of the light beam 28 varies, then the value of the current $I_0$ will likewise vary, decreasing in magnitude if the light intensity decreases. Thus, when the light beam 28 is interrupted by a drop 17, the value of $I_0$ is momentarily reduced significantly thus causing the voltage on the output signal line 32 to increase (with respect to ground) a significant amount (the voltage drop across R1 decreased as $I_0$ decreases, thus raising the voltage at the collector of Q2 towards $+V$). As soon as the drop passes through the light beam 28, and the light beam is restored to its original intensity, then the current $I_0$ is restored to its previous value and the voltage level of the output signal 32 decreases (with respect to ground) to its earlier level. In this fashion a pulse is generated on the signal line 32 when the light beam is interrupted.

The comparator 70 (also labeled as U1 in FIG. 5) performs the function as previously described in connection with FIG. 4. The reference voltage, $V_{Ref}$, is generated by a voltage divider comprised of resistors R2 and R3. The comparator circuit 70 may be a commercially available operational amplifier, such as the LM324 manufactured by National Semiconductor. Its output signal is directed through a coupling capacitor C2 to the first timer circuit 72. The timer 72 may be a commercially available timer, such as the LM556 manufactured by National Semiconductor. A bias network comprised of resistors R7 and R8 is used to translate the level of the input signal for proper triggering of the timer 72. The values of resistor R9 and capacitor C3 are selected to set the time T1 of the external of the output pulse of timer 72 to the desired value.

The output of the timer 72 is directed to a second timer 74 (also labeled as U4 in FIG. 5). This timer may likewise be a commercially available timer, such as the 74123 dual one shot multivibrator manufactured by Texas Instruments, Inc., or numerous other manufacturers. A resistor R14 and capacitor C5 are used to set the time of the pulse generated by this device. The positive output of the timer 74, that is the output on which a positive pulse appears (labled as the Q output in FIG. 5) is sent directly to a binary counter 76, which counter is adapted to be incremented on the negative, or trailing edge, of the pulse T2. This counter 76 may also be a commercially available component, such as the 74393 dual four bit ripple binary counter manufactured by Texas Instruments. When both sides of such a dual four bit counter are connected in series, as they are in FIG. 5, an eight bit counter is realized. The output of the binary counter 76 is directed in parallel to a latch circuit 78. This latch circuit may be a commercially available eight bit I/O port 8212 manufactured by Intel Corp., and designed to be used with the 8080 microprocessor series of components. The latch circuit 78 may thus interface with external instrumentation equipment that can display the count or compute the volume of fluid that has dropped through the device from the count. This computation is achieved through a simple multiplication of the number of drops times the volume of fluid per drop. The counter 76 need never be reset if the external computing equipment is programmed to make and store an initial reading thereof.

The negative output of the second timer 74, labled Q in FIG. 5, is directed through a filter network comprised of resistor R0 and capacitor C0 to the AND gate 80. The function of the gate 80 was described in connection with FIG. 4.

The output of the comparator 70 is directed through an inverter gate 82 to a NOR gate labeled U8. The other input to the NOR gate U8 is the output pulse generated by the timer 72. The output of the NOR gate U8 is connected to the cathode of a diode CR1, which may be a commercially available 1N4005, the anode of which is connected through a pull up resistor R13 to the $+V$ voltage supply. The anode of CR1 is also directed through the cable 54 to an LED diode CR3 located in the drop fixture 22. CR3 may be any commercially available LED, such as the TIL220 manufactured by Texas Instruments. When no drops are falling through the drop chamber 16, both inputs to the NOR gate U8 are low, thus causing the output thereof to be high. With a high output, diode CR1 is back biased, and a current flows through resistor R13, through the cable 54, and to light emitting diode CR3. Diode CR3 serves as the light indicator 71 referred to in FIG. 2. As soon as a drop 17 is sensed, the input signals to the NOR gate U8 will go high, thus causing the output thereof to go low. When this happens, the light emitting diode, or indicator light 71, is current starved because all of the current flows through the now forward biased diode CR1. The effect of this action is to cause the indicator light 71 to "wink" (that is go off) when a drop of fluid 17 passes through the drop chamber 16. Thus, the indicator light 71 serves the function of giving visual feedback to an operator of the drop count apparatus that it is functioning properly.

The output signal 32 from the light detector 26 is also sent to an integrater circuit 36. As with the comparator circuit 70, the integrater circuit 36 may be realized using a commercially available operational amplifier, such as the LM324 manufactured by National Semiconductor. Resistor R4 and capacitor C1 serve to set the time constant associated with the integration process of the device. As mentioned previously, these values are chosen so that the output of the integrator is insensitive to short variations in the input signal, "short" referring to the time it takes a drop to fall through the drop chamber. However, should the input to the integrater 36 indicate a long term variation, then its output signal 44 would reflect this variation. Resistors R5 and R6 are used in connection with the operation of the integrater 36 to provide a reference voltage about which variations in the input signal 32 can be measured.

The output signal 44 of the integrater 36 is used to control the amount of current that is generated in a current source 46, which current is directed through the cable 54 to the light emitter 24 (or CR2). The current source 46 comprises a transistor Q1, such as a 2N3906, connected as shown in FIG. 5. That is, an emitter resistor R10 is connected to the positive voltage supply, +V. The collector of Q1 is connected to the output signal line 30 which is directed to the light emitter 24. A resistor network comprised of resistors R11 and R12 places a reference voltage at the base of Q1 that is proportional to the output voltage of the integrater 44. The voltage across the emitter resistor R10 will be approximately equal to the voltage across the resistor R11 (minus the base emitter voltage drop, $V_{BE}$, of Q1). This voltage across R10 sets the amount of current I that can flow through Q1, and hence it sets the amount of current that can flow through the light emitter 24.

To illustrate the operation of the compensating feature of the invention, consider what happens when the light beam 28 is blocked or impaired by a long term perturbation, such as condensation on the walls of the drop chamber 16, or dirt on the lens 62 of the light emitter 24. If the intensity of the light beam as sensed at Q2 decreases, then the voltage level on the output signal line 32 will increase with respect to ground. This increased voltage will be reflected at the output of the integrater 36 by a decrease in the voltage (with respect to ground) as measured at point 44 due to the integrator's negative gain factor. This decrease in voltage causes the voltage at the base of Q1 to likewise decrease, thus causing more voltage to be dropped across the emitter resistor R10. With more voltage dropped across R10, more current I will flow to the light detector 24, causing the intensity of the light beam 28 to increase so that the amount of light detected at Q2 will eventually reach the point it was before the condensation or other foreign matter caused the intensity to decrease.

An additional feature of the invention herein disclosed is the use of alarms to sense when the cable 54 is not properly connected. That is, when the cable 54 is not plugged in to its proper place, the current that would normally flow to the light emitter 24 will have no place to go since there is an open circuit. When this open circuit exists, it is an easy matter for one skilled in the art to design an alarm circuit that senses this open condition and alerts the operator that an improper configuration is present.

Figure 6:
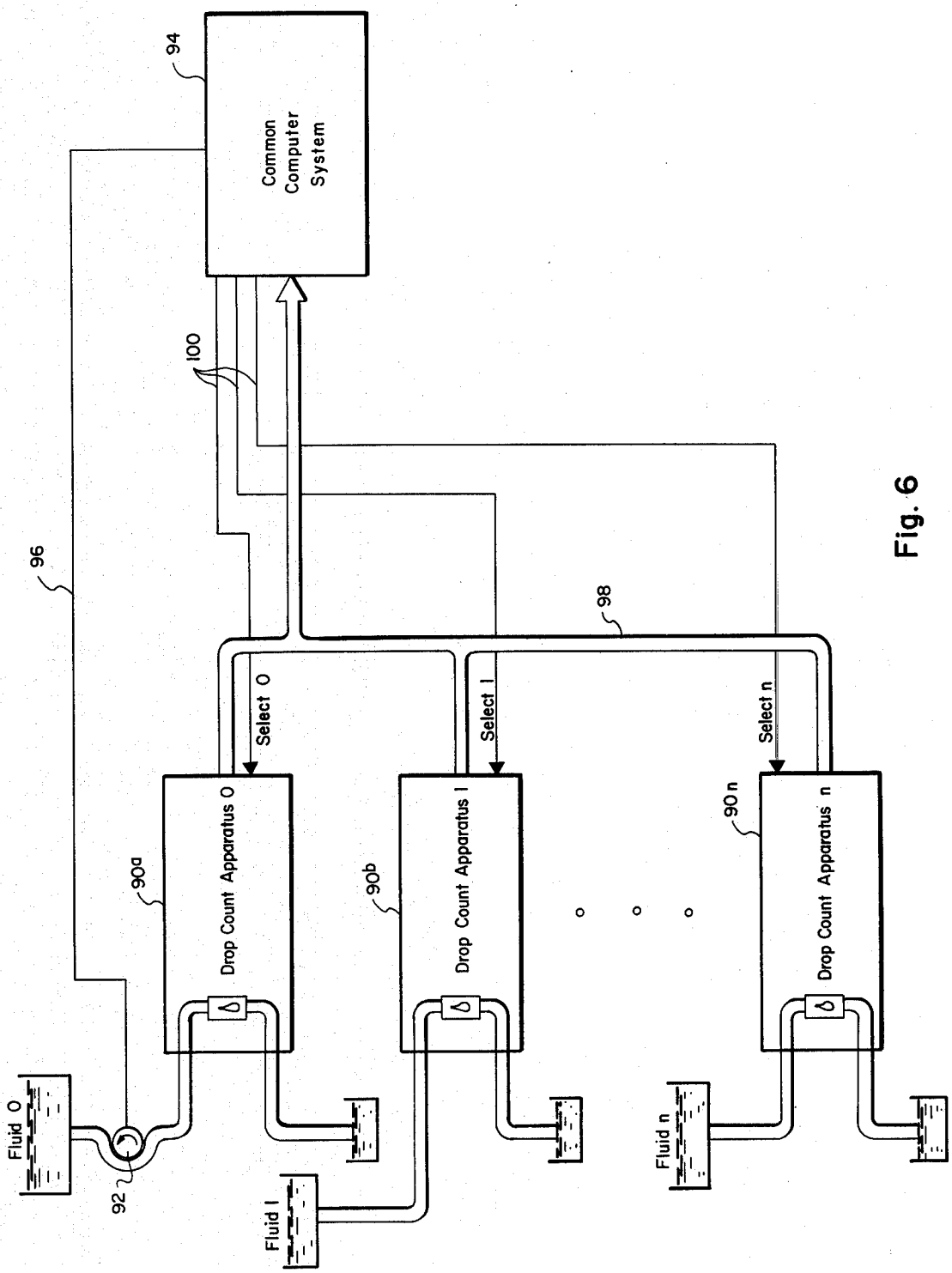
FIG. 6 shows how a plurality of drop count apparatus could be used with a single computing system so as to measure the volume flow of a pluarlity of fluids.

Referring now to FIG. 6, there is shown a plurality of the drop count apparatus used with a single computing system so as to efficiently measure the volume of a plurality of fluids. Such an application could be of extreme importance, for example, in a medical environment where the drop count apparatus are used to measure body fluids flowing to and from a patient. That is, a first drop count apparatus 90a could be used to measure fluid that is being infused into the patient. At the same time, a second drop count apparatus 90b could be used to measure the fluid that is being excreted from the patient. Medical technology dictates that a desired balance be obtained between the fluid infused into the patient verus that which is excreted from the patient. Thus, a common computer system 94 could be used to systematically evaluate the volume going into and coming out of the patient. Accordingly, a control signal could be sent to an infusion pump 92 over a signal line 96 to control the level of infused fluid so as to achieve the desired level of excreted fluid. Similarly, additional drop count apparatus could be used to measure as many fluids as desired. The common computer system 94 would read the latches associated with each drop count apparatus by looking at a common databus 98. Select lines 100 could be sent to each apparatus to indicate which particular drop count was to be measured at a given time.

While the invention disclosed herein is ideally suited for measuring volumetric flow of body fluids of patients in a medical environment, the inventor recognizes numerous other applications where the invention could be used. For example, the flow of liquid fuels from a fuel tank to a combustion chamber could be measured using the invention. Similarly, the volumetric flow of low pressure fluids in a chemical processing plant or research laboratory, or the like, could easily be monitored through a device that incorporates the present inention.

To illustrate the effectiveness and accuracy of the comensated drop count apparatus disclosed herein, the inventor has used the system for measuring both infusion rates of body fluid into a patient and excretion rates of body fluids from the patient. Accuracy of the volume measurement has been within 4% of that measured through the prior art collection systems. The drop count apparatus is ideally suited for a system such as that described in FIG. 6. Such a system for evaluating the over all body fluids of a patient is described more fully in Bowman and Westensckow, "Closed Coop Infusion System Based on Real-Time Urine Measurement," Ser. No. 083027, filed Oct. 9, 1979.

While the invention herein disclosed has been described by means of specific embodiments and applications thereof numerous modifications and variations could be made thereto by those skilled in the art without departing from the spirit and scope of the present invention. It is therefore to be understood that within the scope of the appended claims, the invention may be practiced otherwise than as specifically described herein.

What is claimed is:

1. A self-compensating optical drop count apparatus for measuring volumetric fluid flow comprising:
   (a) a drop chamber including:
      (1) a hollow body, having a radiation transmission path therethrough,
      (2) fluid inlet means coupled to an upper end of said hollow body for allowing a fluid to flow into said hollow body,
      (3) drop formation means coupled to said fluid inlet means for causing said fluid to break up into drops of an approximate uniform volume before said fluid passes through said hollow body, said drop formation means being positioned so that said drops pass through said hollow body along a longitudinal drop path that intersects with said radiation transmission path, and
      (4) fluid outlet means coupled to a lower end of said hollow body for allowing said fluid to flow away from said hollow body after passing therethrough;
   (b) a light emitter adapted to continuously emit a directional light beam along said radiation transmission path, said light beam having an intensity that is controlled by an input control signal to said light emitter;
   (c) a light detector optically coupled with said light beam after said light beam has passed through said hollow body along said radiation transmission path, said light detector being adapted to generate an output signal that indicates the presence and intensity of said light beam at said light detector;

(d) counting means coupled to said output signal of said light detector for counting interruptions that occur in said output signal, said interruptions being caused by said drops of fluid as said drops pass through said hollow body and interrupt said light beam, said counting means including single count protection means for counting only one interruption of a plurality of interruptions occurring in said output signal as a result of one of said drops breaking up into a plurality of smaller drops as it passes through said hollow body, said counting means thus adapted to count the number of drops of said liquid that pass through said chamber, said count, in combination with the approximate known volume of said drops, thus providing a measure of the volumetric flow of said fluid; and (e) compensating means coupled to said output signal of said light detector and said input control signal of said light emitter for compensating the intensity of said light beam as emitted from said light emitter so that the intensity of said light beam as detected at said light detector is maintained at an average constant level regardless of any matter that may, on a long-term basis, tend to block said radiation transmission path.

2. An optical drop count apparatus as defined in claim 1 wherein said compensating means comprises:

(a) an integrator electrically connected to said output signal of said light detector for sensing long-term variations in the intensity of said light beam as detected at said light detector and as reflected in the output signal thereof, and for generating an integrated output signal that is a measure of said sensed variations; and (b) a variable current source electrically coupled to said integrated output signal, said current source adapted to generate an output current whose amplitude is controlled by said integrated output signal, said output current being directed to said light emitter and serving as said input control signal which controls the intensity of said light beam emitted by said light emitter.

3. An optical drop count apparatus as defined in claim 2 wherein said single count protection circuitry of said counting means comprises:

(a) a first timer triggered by an interruption in the output signal of said light detector, said first timer generating a time pulse of $T_1$ seconds, and said first timer being disabled from being triggered during said $T_1$ seconds, said $T_1$ time interval being selectively chosen so as to be longer than the time it takes one of said drops to pass through said light beam;

(b) a second timer triggered by the leading edge of said time pulse of $T_1$ seconds for generating a second time pulse of $T_2$ seconds, where $T_2$ is less than $T_1$; and (c) a counting register coupled to said second time pulse, said counting register adapted to be incremented by the trailing edge of said second time pulse, said counting register thus being incremented once, and only once, for each of said drops that passes through said light beam.

4. An optical drop count apparatus as defined in claim 3 further including a comparator circuit to amplify, buffer and shape said output signal from said light detector before said signal is used to trigger said first timer.

5. An optical drop count apparatus as defined in claim 4 wherein said light emitter comprises an infared light emitting diode through which said output current of said current source flows, said light emitting diode adapted to emit a directional infared light beam with an intensity proportional to said output current.

6. An optical drop count apparatus as defined in claim 5 wherein said light detector comprises a photosensitive transistor adapted to detect the presence and intensity of said directional infared light beam.

7. An optical drop count apparatus as defined in claim 3 wherein said counting register comprises:

(a) an n-bit binary counter, where n is an integrator; and (b) an n-bit holding register, each bit of which is coupled to said n-bit binary counter, said n-bit holding register being adapted to be updated with the count of said n-bit binary counter each time said first and second timers are triggered and to interface said count with external instrumentation equipment adapted to display said count and convert it to a volumetric measure.

8. An optical drop count apparatus as defined in claim 7 further including strobe lockout circuitry for preventing said n-bit holding register from being updated with a new count from said n-bit binary counter coincident with the utilization of said count contained in said n-bit holding register by said external instrumentation equipment.

9. An optical drop count apparatus as defined in claim 8 wherein said external instrumentation equipment comprises computing means electrically connected to said n-bit holding register, said computing means being programmed to convert said count to a volumetric measure of said fluid flow and to automatically display said measure to a user of said apparatus.

10. An optical drop count apparatus as defined in claim 7 further including drop volume compensating means coupled to said n-bit holding registere for compensating the count stored therein, said compensating means adapted to account for changes of volume that occur in said drops as said drops fall at a different rate.

11. An optical drop count apparatus as defined in claims 9 or 10 wherein said computing means comprises a microprocessor based system packaged in a relatively small housing that may be located in close proximity to said drop chamber, thereby allowing said drop count apparatus to be highly mobile.

12. A plurality of drop count apparatus as defined in claims 9 or 10, each of which interfaces with said computing means, thereby allowing a plurality of fluid drop count measurements to be made utilizing a single computing means to convert said drop count measurements to volumetric flow measurements.

13. An optical drop count apparatus as defined in claim 3 wherein said hollow body having a radiation transmission path therethrough comprises a length of hollow tubing having translucent walls.

14. An optical drop count apparatus as defined in claim 13 wherein said translucent walls are transparent.

15. An optical drop count apparatus as defined in claim 3 wherein said hollow body having a radiation transmission path therethrough comprises a length of hollow tubing having transparent windows in opposite walls thereof.

16. An optical drop count apparatus as defined in claim 3 adapted to measure volumetric flow of a body fluid for medical purposes.

17. An optical drop count apparatus as defined in claim 16 wherein said body fluid is urine.

18. An optical drop count apparatus as defined in claim 16 wherein said drop count chamber and associated fluid inlet and outlet means comprise a disposable flow measuring set that may be medically decontaminated, used once, and discarded.

19. A self-compensating method for optically measuring volumetric fluid flow comprising the steps of:
  (a) inserting a drop chamber in series with a tube through which a fluid to be measured is flowing:
  (b) inserting means inside of said tube to break said fluid up into drops of an approximate uniform known volume before said fluid passes through said drop chamber along a drop path;
  (c) optically coupling a light emitter that emits a beam of light, with a light detector, that generates an output signal which indicates the presence and intensity of said beam of light as detected at said light detector, through a light transmission path that passes through said drop chamber and intersects said drop path;
  (d) compensating the intensity of said light beam as emitted by said light emitter so that the intensity of said light beam as detected at said light detector is maintained at a constant level regardless of any matter that might on a long-term basis optically interfere with said light beam along said light transmission path;
  (e) monitoring said output signal of said light detector for pulses, said pulses indicating the absence of said light beam and thus indicating that said light beam has been interrupted by said drops as said drops pass through said drop chamber;
  (f) electrically counting the number of pulses that occur in said output signal in such a way that one count is assigned to each drop of fluid that passes through said drop chamber; and
  (g) converting the number of pulses thus counted to a volumetric measurement by multiplying the number of pulses, which corresponds to the number of drops of fluid that have passed through the drop chamber, by the compensated volume of each drop, said compensated volume being determined by monitoring the rate at which said drops fall through said chamber, a larger volume assigned to drops that fall at a fast rate, and a smaller volume assigned to drops that fall at a slower rate.

* * * * *